United States Patent [19]

Sachse

[11] Patent Number: 4,713,058
[45] Date of Patent: Dec. 15, 1987

[54] GUIDING MANDRIN FOR DRAINAGE DUCTS

[75] Inventor: Hans-Ernst Sachse, Lerchenstrasse 55, 8500 Nuremberg 90, Fed. Rep. of Germany

[73] Assignee: Hans-Ernst Sachse, Nuremberg, Fed. Rep. of Germany

[21] Appl. No.: 844,675

[22] Filed: Mar. 27, 1986

[51] Int. Cl.⁴ .............................................. A61M 5/00
[52] U.S. Cl. .................................... 604/165; 604/170; 128/657
[58] Field of Search ................. 604/165, 164, 170, 93, 604/104, 107, 264; 128/DIG. 26, 658, 657

[56] References Cited

U.S. PATENT DOCUMENTS

| | | | |
|---|---|---|---|
| 2,586,940 | 2/1952 | Graham | 128/DIG. 26 |
| 4,148,319 | 4/1979 | Kasper et al. | 604/170 |
| 4,248,234 | 2/1981 | Assenza et al. | 604/170 |
| 4,249,541 | 2/1981 | Pratt | 604/165 |
| 4,502,482 | 3/1985 | DeLuccia et al. | 604/165 |

Primary Examiner—Stephen C. Pellegrino
Attorney, Agent, or Firm—Keil & Weinkauf

[57] ABSTRACT

Guiding mandrin for drainage ducts featuring a wedge that by being pushed in or pulled out of the split tip of the mandrin tube will cause said tip to increase or reduce its diameter according to requirement. Hereby, a firm contact between guiding mandrin and drainage duct can be established which will significantly facilitate the handling of the drainage duct.

5 Claims, 4 Drawing Figures

GUIDING MANDRIN FOR DRAINAGE DUCTS

Drainage ducts made from elastic material have long been known in medical practice. They serve for keeping constricted body organs open thus allowing the passage of body fluids or of irrigation liquids from one cavity to another or to the outside, respectively.

A very frequent application for such drainage ducts is the ducting of the ureter, where urine is ducted from the renal pelvis into the bladder, or where the drainage ducting also bridges the urethra and passes the urine to the outside. Here, drainage ducts with a tip that does not slide out of the renal pelvis but retains itself there due to its curved configuration have proven particularly successful. To introduce such drainage ducts which are known as pigtail ducts on account of their shape, the bending of the tip must be compensated by a relatively rigid guiding mandrin. This mandrin has to fulfill yet another task.

Generally, one end of the drainage duct lies in the renal pelvis with the other end in the bladder. A cystoscope is used to insert such a duct. In order to place the relatively short drainage duct into the ureter, a second auxiliary duct is necessary which is also pushed onto the guiding mandrin after the drainage duct has been threaded on in order to assure satisfactory introduction of the drainage duct. During the introduction process this will furthermore eliminate the frequently existing bend at the end of the drainage duct which is to prevent that the end of the drainage duct disappears into the ureter and does no longer project from the ureteral orifice, a complication not easily remedied.

Up to now it has been necessary during introduction to press the end of the drainage duct as well as the end of the auxiliary duct against the guiding mandrin by means of strong clamps and thus fix it for insertion. These relatively large and heavy clamps may considerable encumber the surgeon's work.

After the drainage duct has been introduced into the lower part of the ureter via urethra and bladder by means of a cystoscope, the end of the drainage duct will disappear in the urethral orifice, and the clamp positioned here must be removed. This will cancel the firm connection between drainage duct and guiding mandrin. From tihs moment, the drainage duct can only be pushed forward into the direction of the renal pelvis.

With each attempt to retract the drainage duct or to turn it, the drainage duct will detach itself from the guiding mandrin and remain in the ureter and bladder, from where it must now be removed with the help of gripping forceps. Such turning and retracting movements of the drainage duct can often not be avoided due to the frequently irregular ureter tracts. It is the task of the auxiliary duct to provide stiffness for the guiding mandrin where it is not surrounded by the drainage duct, and to support the drainage duct while the guiding mandrin is pulled out, i.e. it must assure that, when the guiding mandrin is pulled out after complete introduction of the drainage duct, this in not being pulled out again.

An object of the present invention is to firmly connect the tip of the guiding mandrin with the tip of the drainage duct by enlarging the diameter of the tip of the guiding mandrin as required, so that retracting and turning movements can be carried out easily and without problems. By reducing the diameter of the tip of the guiding mandrin, the firm connection with the drainage duct is again released, and the guiding mandrin can be pulled out easily.

In an embodiment of the invention the enlargement of the diamter of the guiding mandrin tip takes place by pushing a wedge into the single- or multiple-split tip of the guiding mandrin, thus expanding its elastic wall. Wedge movement is controlled by the movement of the wedge push-pull wire projecting from the mandrin tube.

In the reverse sense, the tip of the guiding mandrin is narrowed by removing the wedge from the expanded tip of the mandrin tube, whereupon said tip is then reduced to its original size due to its intrinsic elasticity and the pressure exerted by the surrounding tissue, thereby releasing the firm connection to the inner wall of the drainage duct. As in the customary system, the removal of the guiding mandrin is facilitated by using a second auxiliary duct which pushes against the shorter drainage duct during the removal. As soon as the tip of the guiding mandrin has passed the contact area between drainage duct and auxiliary duct during removal, the two ducts will detach themselves from each other, and the drainage duct will remain in the bladder with one end projecting from the ureteral orifice. The auxiliary duct will then be completely removed together with the guiding duct. The present invention no longer requires fixation of drainage duct and auxiliary duct to the guiding mandrin by means of heavy clamps.

Fixation of the wedge in the tip of the mandrin tube is effected by the continuous, tension applied by the wedge push-pull wire which is pressed against the inner wall of the maindrin tube end with the aid of a conical retaining needle, thus assuring its fixation.

Unlike in the previous systems, the guiding mandrin according to the invention does not need to find a sort of abutment at the front end of the inner wall of the drainage duct while said drainage duct is moved forward during introduction, so that the tip of the drainage duct can have a central lumen and the drainage duct is better able to fulfill its function.

Fixation fixation of the wedge push-pull wire at the end of the mandrin tube is effected by means of a clamping device. Two plastic or metal plates with a smooth or fluted surface are connected by means of a hinge or an elastic bend and can be pressed against each other by means of a screw, thereby retaining the end of the mandrin tube between themselves. As known from similar commercially available products, the clamping process can also be carried out manually, whereby the two plate ends will engage into a latching device when clamped.

The clamping of the mandrin end is effected by means of a commercially available tube pinch, in which two parallel plates provided with guiding rods are pressed against each other by means of a screw.

BRIEF DESCRIPTION OF THE DRAWINGS

The subject of the invention is illustrated by the embodiments of the invention represented in the drawings in which.

FIG. 1 represents a longitudinal section of the drainage duct tip and the tip of the guiding mandrin. The guiding mandrin 1 consists of the guiding mandrin tube 10 which is provided with a split area 6 in the tip 4 of the guiding mandrin. The wedge 7 can be pushed into the split tip 4 of the guiding mandrin and will expand said tip 4 of the guiding mandrin which consists of an elastic material, thereby increasing its diameter. The motion of the wedge 7 is controlled by the wedge push-pull wire 8 which is firmly connected with the wedge 7.

As shown in FIG. 1, the tip of the guiding mandrin is located in the area of the tip 2 of the drainage duct where it can clamp itself to the inner wall of the drainage duct while the wedge is in its pulled-in state as shown in FIG. 4.

FIG. 2 represents a longitudinal section of the end 2 of the auxiliary duct and the end 5 of the mandrin tube. In this embodiment of the invention, the wedge push-pull wire 8 is pressed against the inner wall of the mandrin tube end 5 by the retaining needle 9 and thus fixed in this position.

FIG. 3 shows a cross section of a pinch clamp and the end of the guiding mandrin. The pinch clamp consists of the two plates 13 which are connected by hinge 11 and belt 12, and which can be pressed against each other by means of the screw 14. The two plates retain the end of the mandrin tube between themselves and press its walls against the wedge push-pull wire 8.

FIG. 4 shows the location of drainage duct and auxiliary duct relative to the guiding mandrin 1. For introduction, drainage duct 2 as well as auxiliary duct 3 are guided. The guiding mandrin has now clamped its tip 4 against the tip of the drainage duct after having pulled in the wedge 7.

Figure 1:
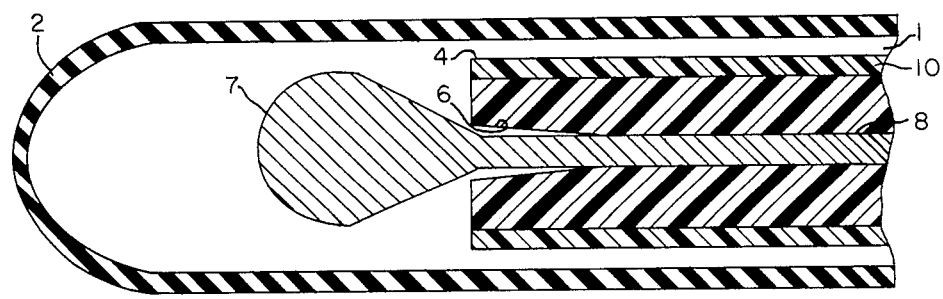
FIG. 1 shows a longitudinal section of the tip of the drainage duct and the tip of the guiding mandrin.
Figure 2:
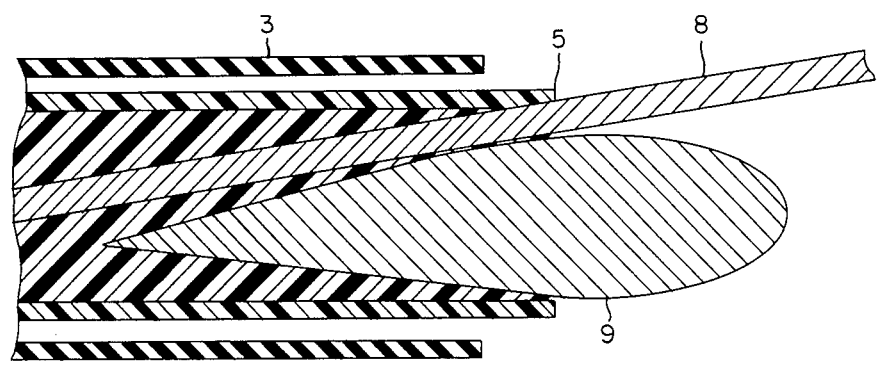
FIG. 2 shows a longitudinal section of the end of the auxiliary duct and the end of the guiding mandrin.
Figure 3:
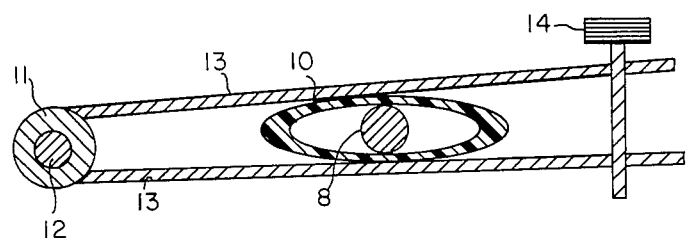
FIG. 3 shows a cross section of the end of the guiding mandrin with a pinch clamp.
Figure 4:
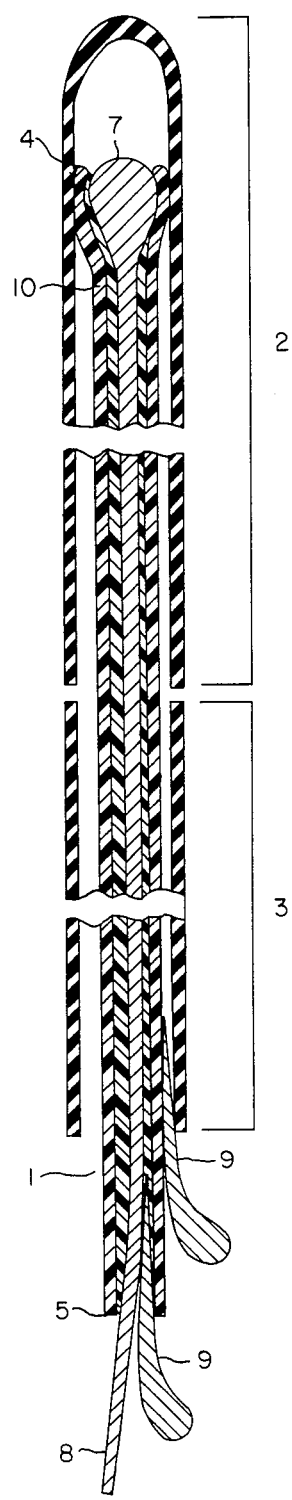
FIG. 4 shows a longitudinal section of drainage duct, auxiliary duct, and guiding mandrin.

The auxiliary duct 3 has been inserted up to the end of the drainage duct 2. Its end is fixed to the guiding mandrin by means of a retaining needle 9 clamped between outer wall of guiding mandrin and inner wall of auxiliary duct 3. The wedge push-pull wire 8 projecting from the mandrin tube end 5 is fixed by means of a second retaining needle clamped between wedge push-pull wire 8 and inner wall of mandrin tube.

Index Numbers

1 Guiding mandrin
2 Drainage duct
3 Auxiliary duct
4 Tip of mandrin tube
5 End of mandrin tube
6 Split tip of mandrin tube
7 Wedge
8 Wedge push-pull wire
9 Retaining needle
10 Mandrin tube
11 Hinge of pinch clamp
12 Hinge bolt
13 Plates of pinch clamp
14 Screw

I claim:
1. A guiding mandrin for insertion into a drainage duct comprising:
   a long horizontal tube made of elastic material or from flexible resilient metal wherein the tip of said tube is split,
   and a wedge push-pull wire passes through the entire length of said tube and extend beyond both ends thereof, said wire having a wedge means firmly attached to said wire end extending beyond the tip end of said tube, the diameter of the wedge means being greater than the diameter of said tube,
   whereby the split end of said tube is forced outwardly to engage the inner wall of the drainage duct by manipulating said wire so as to move the wedge means into the split end of said tube and is disengaged from said wall by moving the wedge means out of the split end of said tube.

2. A guiding mandrin according to claim 1 wherein a conical fixation needle is located in between the wedge push-pull wire and the inner tube wall at the other end of the mandrin.

3. A guiding mandrin according to claim 1 wherein the inner tube wall in the region of the other end of the tube is pressed against the wedge push-pull wire by positioning the tube end between two plates with smooth or fluted surfaces and connected by means of a hinge, which is pressed together with the aid of a screw.

4. A guiding mandrin according to claim 1 wherein the inner tube wall in the region of the other end of the tube is pressed against the wedge push-pull wire by positioning the tube end between two parallel plates provided with guiding rods, which are pressed against each other by means of a screw.

5. A guiding mandrin according to claim 1 inserted into an auxiliary duct and a drainage duct placed end-to-end wherein the free end of the auxiliary duct is fixed to said tube by a retaining needle means clamped between the outer wall of said tube and the inner wall of the auxiliary duct.

* * * * *